United States Patent [19]

Rach et al.

[11] Patent Number: 5,753,047
[45] Date of Patent: May 19, 1998

[54] METHOD, WASHER APPARATUS AND CLEANING AGENT FOR CLEANING A GLASS WINDOW OF A MOTOR VEHICLE

[75] Inventors: Elmar Rach, Ditzingen-Heimerdingen; Klaus Brill, Korntal-Muenchingen, both of Germany

[73] Assignee: Robert Bosch GmbH, Stuttgart, Germany

[21] Appl. No.: 909,128

[22] Filed: Jul. 6, 1992

Related U.S. Application Data

[63] Continuation of Ser. No. 712,129, Jun. 6, 1991, abandoned.

[30] Foreign Application Priority Data

Jun. 20, 1990 [DE] Germany .................. 40 19 588.0

[51] Int. Cl.$^6$ ........................................ B08B 7/04
[52] U.S. Cl. ...................... 134/7; 134/26; 134/32; 134/36
[58] Field of Search .................. 134/6, 7, 26, 32, 134/36, 38; 15/250.36, 250.4, 250.41, 250.04

[56] References Cited

U.S. PATENT DOCUMENTS

| | | | |
|---|---|---|---|
| 2,780,568 | 2/1957 | Clark | 134/7 |
| 3,407,426 | 10/1968 | Muller | 15/250.04 |
| 3,631,561 | 1/1972 | Aszkenas | 15/250.41 |
| 4,045,838 | 9/1977 | Porter | 15/250.36 |
| 4,103,385 | 8/1978 | Porter | 15/250.36 |
| 4,106,915 | 8/1978 | Kagawa et al. | 51/296 |
| 4,343,116 | 8/1982 | Murphry et al. | 134/27 |
| 4,628,565 | 12/1986 | Wolters | 15/250.41 |
| 4,649,593 | 3/1987 | Gilliam, III et al. | 15/250.41 |
| 4,716,618 | 1/1988 | Yasukawa et al. | 15/250.36 |
| 4,719,661 | 1/1988 | Hanselmann | 15/250.41 |
| 4,745,653 | 5/1988 | Bilznak | 15/250.36 |
| 4,754,517 | 7/1988 | Aldous | 15/250.41 |

FOREIGN PATENT DOCUMENTS

| | | | |
|---|---|---|---|
| 2725405 | 12/1978 | Germany | B60S 1/38 |
| 3838904 | 6/1990 | Germany | B60S 1/38 |
| 4019588 | 1/1992 | Germany | B60S 1/38 |
| 2004458 | 4/1979 | United Kingdom . | |

*Primary Examiner*—Timothy McMahon
*Assistant Examiner*—Saeed Chaudhry
*Attorney, Agent, or Firm*—Michael J. Striker

[57] ABSTRACT

In a process for cleaning a glass window of a motor vehicle with a wiper apparatus having a wiper, including applying a washer fluid including a cleaning agent and water to the glass window from a container located in the motor vehicle, and moving the wiper over the glass window with the wiper apparatus to at least partially clean the glass window with the washer fluid, the improvement includes spraying or blowing a polishing composition containing a metal oxide powder on the glass window, advantageously from a container located in the motor vehicle, and cleaning the glass window with the polishing composition containing the metal oxide powder by action of the wiper together with the polishing composition, so that, when present on the glass window, a hydrophobic dirt layer formed on the glass window is removed. The metal oxide powder advantageously has a particle size from 10 nm to 1 micrometer and is cerium oxide. The polishing composition may be an aqueous suspension which is added to the washer fluid in the vehicle washer apparatus or may be stored in a separate container in the vehicle. The metal oxide powder advantageously has a particle size from 10 nm to 1 micrometer and is cerium oxide.

26 Claims, 2 Drawing Sheets

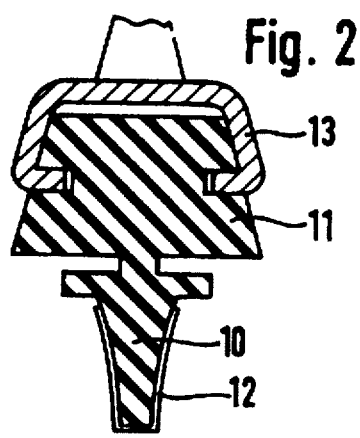
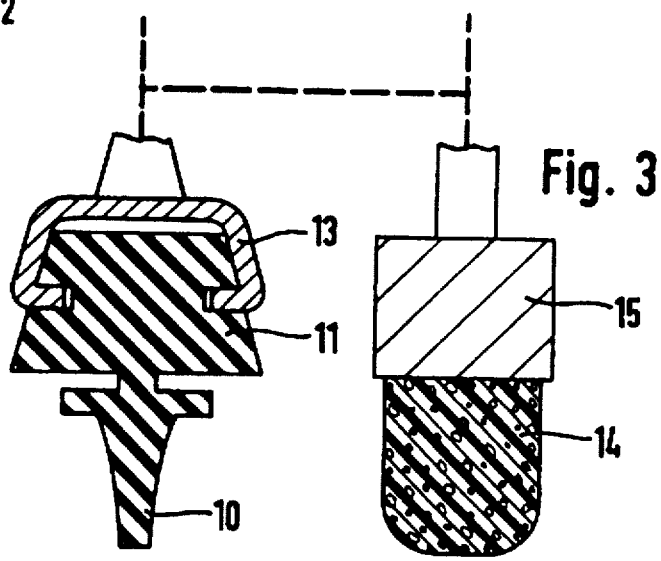
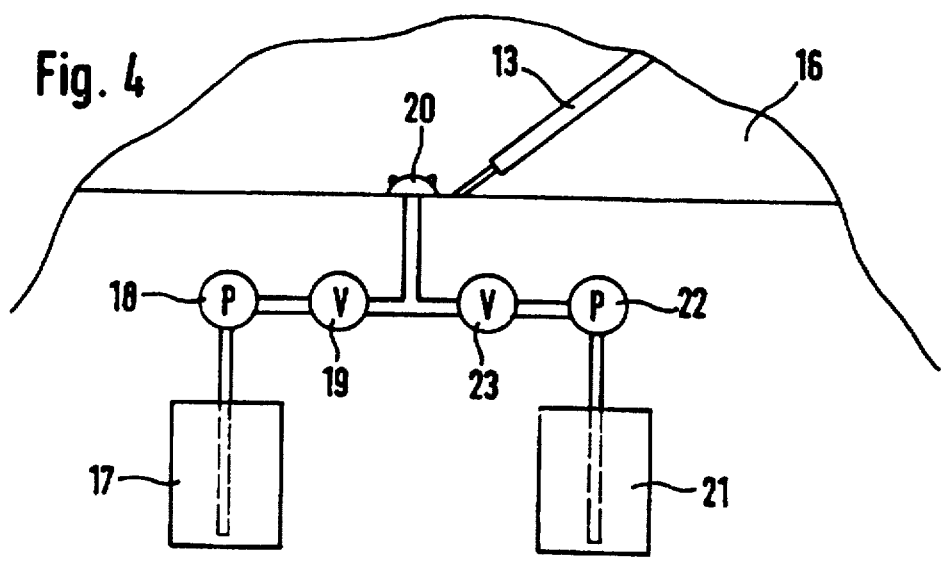

METHOD, WASHER APPARATUS AND CLEANING AGENT FOR CLEANING A GLASS WINDOW OF A MOTOR VEHICLE

This application is a continuation of application Ser. No 712,129, filed Jun. 6, 1991 now abandoned.

BACKGROUND OF THE INVENTION

Our invention relates to a method for cleaning a glass window, over which a wiper moves, particularly a motor vehicle front or rear window. It also relates to a windshield washer apparatus and cleaning agent for performing the process.

In the known method for cleaning a glass window, especially in a motor vehicle, water and a cleaning agent are applied to the glass by a washer apparatus.

On motion of a windshield wiper over a wet glass window pane, a thin water film remains behind the wiper lip and/or the wiper blade. In practice, particularly in motor vehicle operation, a well cleaned and, because of that hydrophilic, window surface is already hydrophobic after a short time because of dirt deposits. A layer only a few molecules thick on the window surface already completely changes the properties of the glass surface. The hydrophobic materials causing this change include dirt from the road, exhaust gases, insects, paint preservative materials and other sources. The hydrophobic materials cause the water film behind the wiper blade to be broken up into fine droplets, which, because of light scattering, can lead to considerable impairment of visibility. These hydrophobic thin layers are extraordinarily adherent and are not removed in vehicle operation with known methods. However grease and dirt dissolving substances can be added to the washer fluid. These additives can, of course, lead to a some improvement in visibility, however only a relatively short time is necessary to cover the window surface with a thin hydrophobic layer of dirt. These adherent hydrophobic substances are not removed, even when grease and dirt solubilizing additives are in the washer fluid.

SUMMARY OF THE INVENTION

It is an object of the present invention to provide an improved method of cleaning a glass pane, especially a window of a motor vehicle, over which a wiper moves, not having the above mentioned disadvantages.

According to the invention, in the method for cleaning a glass window of a motor vehicle with a wiper apparatus having a wiper, including the steps of applying a washer fluid including a cleaning agent and water to the glass window and moving the wiper over the glass window with the wiper apparatus to at least partially clean it, the improvement includes spraying or blowing a polishing composition containing a metal oxide powder on the glass window or applying an aqueous suspension of the metal oxide powder, preferably from a container located in the motor vehicle, to the glass window; and cleaning the glass window with the aqueous suspension or polishing composition by action of the wiper together with the aqueous suspension or polishing composition on the glass window, so that, when present on the glass window, a hydrophobic dirt layer formed on the glass window is removed.

Advantageously, the polishing composition consists essentially of a metal oxide, such as Cerium oxide, having a powder particle size from 10 nm to 1 micrometer.

The method according to the invention has the advantage that the hydrophobic dirt or dust materials are removed during the washing process by a polishing process, so that the glass surface is again hydrophilic and the breaking up of the water film into fine droplets is prevented. Thus, a noticeable improvement of visibility can also be attained for a longer duration, during operation of the motor vehicle. Since the hydrophobic layers are removed and cover the window only for a short time, extended action maintains a clean window despite the presence of materials that can cause hydrophobic dirt formation.

The glass polishing composition used as cleaning agent can be added in the form of a suspension to the washer fluid, whereby only small changes in the usual window washer apparatus are necessary. It is however also advantageously possible to spray or blow the glass polishing composition or agent in suspension, powder or paste form on the window pane from a separate unit. Separate supply containers for cleaning agents are similar to those already provided in different motor vehicles, so also here the present structure of the window washer units can be utilized.

An especially reliable and uniform application of glass polishing composition can be attained, when the lip of the windshield wiper is provided with the glass polishing composition and is applied to the glass window pane by it. Because of that the tip of the windshield wiper can either contain the windshield wiper or it can be coated on the window in a repeatable way automatically or manually from a tube or flask. This type of manual application can occur directly on the glass window pane. The application of the polishing agent layer to the lip forming the rubber wiper lip can occur by coating, brushing, spraying or immersion. The connection of a powdery polishing composition to the rubber wiper lip can occur by pressing the powder in or by rolling it in. Also the polishing composition can be included mechanically or thermally in the outer portion of the rubber wiper lip. Understandably the rubber wiper lip can also be made of a mixture of rubber material and glass polishing composition. A fresh portion of glass polishing composition is always provided automatically by wear of the rubber wiper lip. The lip carrying the glass polishing agent can also be formed as a separate additional polishing lip, which can be arranged separately on a separate polishing washer apparatus. In this latter device, the individual rubber washer lip for the washer process can be optimized separately from the polishing lip for the polishing means. For example, the polishing lip can be a separate foam strip.

BRIEF DESCRIPTION OF THE DRAWING

The objects, features and advantages of the present invention will now be illustrated in more detail by the following detailed description, reference being made to the accompanying drawing in which:

FIG. 2 is a transverse cross sectional view through a coated windshield wiper lip according to the invention;

FIG. 3 is a transverse cross sectional view through a conventional windshield wiper lip and a separate polishing lip according to the invention, and FIG. 4 is a schematic diagram of a window cleaning apparatus according to the invention having separate supply containers for washer fluid and polishing agent.

DETAILED DESCRIPTION OF THE INVENTION

Figure 1:
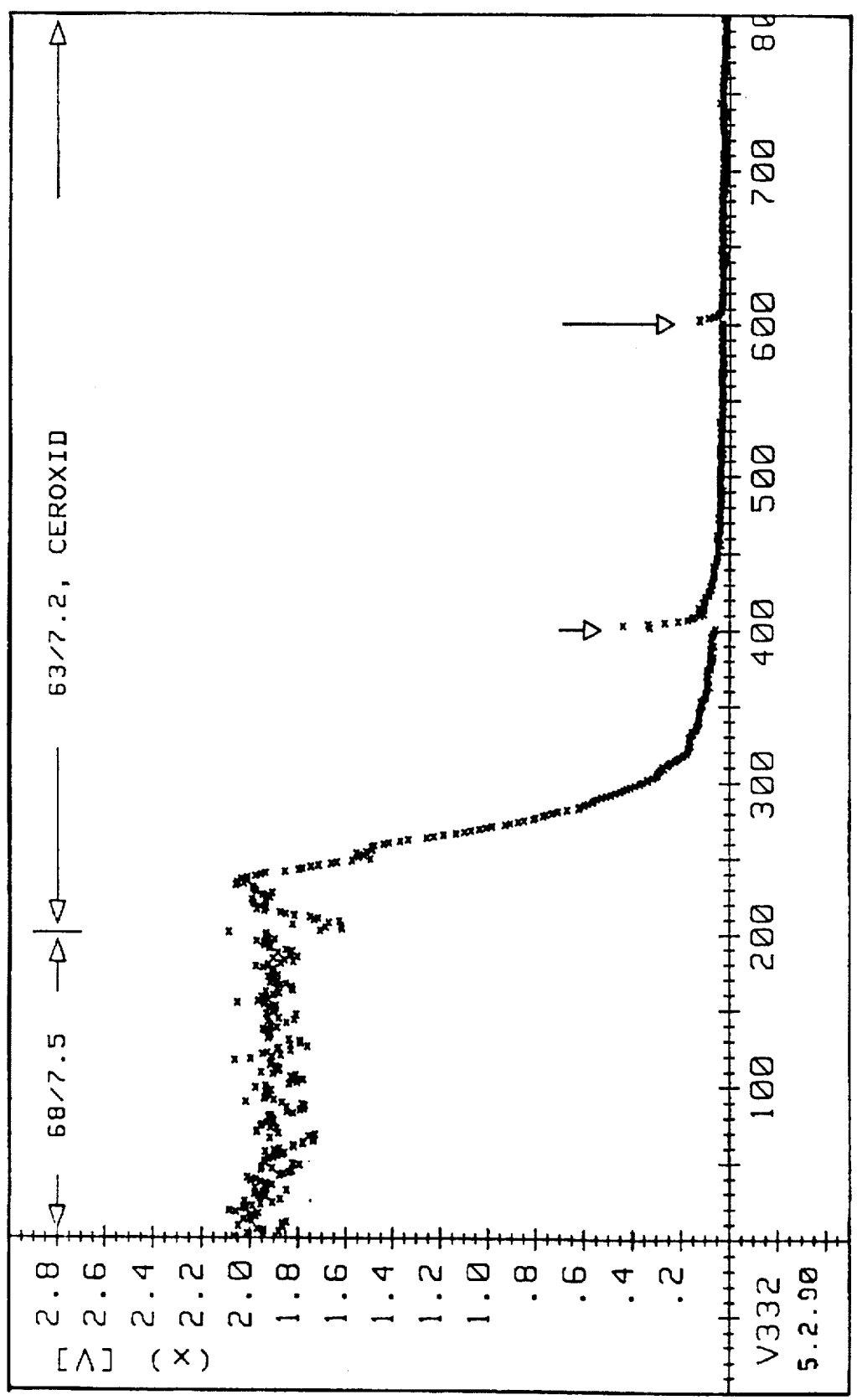
FIG. 1 is a graphical illustration of comparative results of a light scattering test of the method according to the invention with and without cerium oxide polishing agent application.

The crux of the invention is that the hydrophobic substances adhering on the window surface are to be removed by a polishing agent suitable for a glass surface and to maintain a hydrophilic window pane surface, on which the thin water film remaining behind the rubber wiper of the windshield wiper is not broken up into droplets. Thus a good, cloudiness-free visibility through the window is obtained. Suitable glass polishing agents include various standard metal oxides, such as $Fe_2O_3$, $Fe_3O_4$, $Al_2O_3$, $Cr_2O_3$, $CeO_2$, $ZrO_2$, $TiO_2$, $SnO_2$, $SiO_2$. Cerium oxide($CeO_2$) has been to be the most effective of these substances.

The polishing method for the glass surface is a complimentary process. The action of the polishing agent is based on a combination of mechanical material removal, plastic deformation of the surface layer and chemical action. In the tribochemical frictional wear polishing theory, a local "welding" of the polishing grains with the glass surface is postulated, and because of that molecular removal occurs at the "welded" locations by tearing away. In polishing processes four components are involved: the glass surface, the polishing agent, the fluid suspension and the polishing agent carrier or applicator. Because of this the cleaning action can be optimized with minimal glass wear considering the friction speed, the pressure, the hardness of the polishing agent carrier or applicator and the mean particle size of the polishing agent. For practical applications, a particle size in the vicinity of from 10 nm to 1 micrometer appears to be especially satisfactory.

Experiments have clearly shown the cleaning action of the glass polishing agents on hydrophobic glass surfaces. In a single wash cycle (spray application of water, and washer motion of the windshield washer), the light scattering intensity as a measure of the droplet scattering for droplets formed on the window was measured, and thus indirectly the extent of the window hydrophobic material. Cerium oxide was used as the glass polishing agent. FIG. 1 shows the behavior of the scattering amplitude after a number of wiper cycles on the hydrophobic window pane. The hydrophobic material was produced by application of silicone oil and subsequent rubbing with a paper towel on the glass window. The hydrophobicity of the window surface is directly apparent at large contact angles, which results in water droplets on the surface of the window.

During the first two hundred wiping cycles a mean light scattering amplitude of about 1.9 volts was measured at standard conditions (rubber wiper hardness, 68 shore; blade dimension, 7.5 mm; application force (normal), 16 N/m; friction speed, 2 m/s; and blade angle, 0°). After two hundred washing cycles the measurements were halted and a new wiper blade (63 Shore, blade dimension, 7.2 mm) was installed, whose lip was coated with Cerium oxide suspended in water.

During the subsequent wiper motion the light scattering amplitude fell quickly to a very small value. The subjective observation with naked eye showed that the cloudiness completely vanished, water drops spread on the glass surface (contact angle about 0°).

A portion of silicone oil, which was sprayed after the four hundredth and the six hundredth cycle, caused light scattering for only a brief time. During an additional eight hundred wiper cycles the windshield surface remains hydrophilic. In this comparative experiment, one must realize that conditions are extreme since pure silicone oil is being sprayed on the window. This is an extreme type of visibility-impairing windshield coating, which would not be expected in practice in the working motor vehicle.

The cerium oxide polishing agent may be applied in several different ways. According to FIG. 2 a wiper lip 10 is provided with a layer 12 of cerium oxide on the rubber wiper blade 11. The rubber wiper blade 11 is attached to a wiper arm 13 in the standard way which is only indicated in part in the drawing.

The layer 12 made from cerium oxide or another metal oxide and/or glass polishing agent can be applied to the wiper lip 10 by coating, brushing, spraying or by dipping or the like. This can occur during the rubber wiper manufacture, e.g. in graphitizing, or in place of graphitizing. Cerium oxide powder can also be subsequently imbedded in the rubber surface with or without heat application, e.g. by a rolling or pressing process. An additional possibility consists in that, after the molding, however prior to the cutting, cerium oxide is shot into the surface by an injection process with high mechanical and/or thermal energy, similar to ion implantation. Understandably, the rubber material of the rubber wiper blade 11 already can be mixed with cerium oxide and/or glass polishing agent in its manufacture.

According to the embodiment shown in FIG. 3, a separate polishing lip can also be provided. The polishing lip can comprise a foam strip. Also other materials can be used. This foam strip is already formed, so that a larger amount of glass polishing agent can be applied during the washing process, which is applied in the foam material of similar applicator or as a layer. The polishing lip 14 is attached to a retaining strip 15, which is a part of the standard windshield wiper or it can be formed as a separate polishing wiper, which can be operated for intensive cleaning.

Cerium oxide can also be sprayed on or blown on the windshield in the form of a suitable suspension, in a suspension in the washer fluid and/or as a powder from a separate supply container. This is shown schematically in the embodiment of FIG. 4. A wiper arm 13 moves over the glass window pane 16 in a washing process, e.g. the front and rear window pane of a motor vehicle. Washer fluid contained in a first supply container 17 is supplied by a pump 18 via a nonreturn valve 19 of a spraying device 20. A second container 21 is provided for a suspension of cerium oxide. This suspension of cerium oxide is suppled by a second pump 22 and a second nonreturn valve 23 of the spraying device 20. By selection or simultaneous operation of the pumps 18,22 either only windshield washer fluid or additionally the cerium oxide suspension can be sprayed on the windshield 16 for cleaning it.

In a known way understandably a single pump and two valves can be provided in both pipes or lines to both containers. Separate jet and/or spray nozzles can be provided, whereby the second container can also contain powdery cerium oxide, which is sprayed on the windshield by a suitable nozzle. It is also possible to supply powdery cerium oxide to the washer fluid in the washer line by a valve.

Many possible combinations of the features described above are possible. For example, instead of the rubber wiper blade with the coated wiper lip the cerium oxide can be applied suspended in washer fluid. The essential feature is that the glass polishing agent must be applied to the window pane and then the polishing process is performed.

An additional possibility is that the glass polishing agent can be applied in pasturized form, especially cerium oxide, in a tube or in suspended from in a flask. The glass polishing agent is then directly manually distributed on the window, the wiper lip or additional polishing blade, also coated. Subsequently, the wiper lip performs the polishing process, whereby understandably an additional manual polishing process occurs on the glass. An auxiliary substance can be used to aid application of the glass polishing agent on the wiper lip of the windshield wiper blade. This can be in the form of a sponge-like material or another form for better application and distribution of the glass polishing agent.

It will be understood that each of the elements described above, or two or more together, may also find a useful application in other types of constructions differing from the types described above.

While the invention has been illustrated and described as embodied in a method, washer apparatus and cleaning agent for cleaning a glass pane, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

We claim:

1. In a process for cleaning a glass window of a motor vehicle with a wiper apparatus having a wiper, said process comprising the steps of applying a cleaning agent and water to said glass window and moving said wiper over said glass window with said wiper apparatus to at least partially clean said glass window with the cleaning agent and water, the improvement comprising the steps of:
   a) spraying a polishing composition containing a metal oxide powder on said glass window; and
   b) cleaning said glass window with said polishing composition containing said metal oxide powder by action of said wiper together with said polishing composition containing said metal oxide powder on said glass window, so that, when present on said glass window, a hydrophobic dirt layer formed on said glass window is removed.

2. The improvement as defined in claim 1, wherein the polishing composition is an aqueous suspension containing the metal oxide powder.

3. The improvement as defined in claim 2, further comprising storing a washer fluid including the cleaning agent and the water in a container in the motor vehicle before the applying of the cleaning agent and the water to the glass window and adding said aqueous suspension to the washer fluid so that said aqueous suspension of the metal oxide powder is sprayed on the glass window at the same time as the washer fluid is applied to the glass window.

4. The improvement as defined in claim 1, wherein said polishing composition consists of said metal oxide powder and said metal oxide powder consists essentially of cerium oxide powder.

5. The improvement as defined in claim 1, wherein said metal oxide powder is selected from the group consisting of $Fe_2O_3$, $Fe_3O_4$, $Al_2O_3$, $Cr_2O_3$, $CeO_2$, $ZrO_2$, $TiO_2$, $ZrO_2$, $TiO_2$, $SnO_2$, $SiO_2$ powders and having a particle size from 10 nm to 1 micrometer.

6. The improvement as defined in claim 1, wherein the applying of the polishing composition to the window also occurs by action of the wiper.

7. The improvement as defined in claim 1, wherein said spraying of the polishing composition is performed at the same time as said applying of the cleaning agent and the water to the glass window with said wiper apparatus.

8. The improvement as defined in claim 1, wherein said spraying of the polishing composition on the glass window and said applying of the cleaning agent and the water to the glass window are preformed at different times.

9. The improvement as defined in claim 1, further comprising storing a washer fluid including the cleaning agent and the water in one container and storing the polishing composition in another separate container in the motor vehicle prior to the applying of the cleaning agent and the water to the glass window and before the spraying of the polishing composition on the glass window.

10. The improvement as defined in claim 1, wherein the polishing composition is distributed manually on a wiper lip of a wiper blade of the wiper from one of a flask and a tube.

11. The improvement as defined in claim 1, wherein the polishing composition is distributed manually on a wiper lip of a wiper blade of the wiper from one of a flask and a tube.

12. In a process for cleaning a glass window of a motor vehicle with a wiper apparatus having a wiper, said process comprising the steps of applying a cleaning agent and water to said glass window and moving said wiper over said glass window with said wiper apparatus to at least partially clean said glass window with the cleaning agent and the water, the improvement comprising the steps of:
   a) blowing a polishing composition containing a metal oxide powder on said glass window; and
   b) cleaning said glass window with said polishing composition containing said metal oxide powder by action of said wiper together with said polishing composition containing said metal oxide powder on said glass window, so that, when present on said glass window, a hydrophobic dirt layer formed on said glass window is removed.

13. The improvement as defined in claim 12, wherein said metal oxide powder is selected from the group consisting of $Fe_2O_3$, $Fe_3O_4$, $Al_2O_3$, $Cr_2O_3$, $CeO_2$, $ZrO_2$, $TiO_2$, $SnO_2$, $SiO_2$ powders and having a particle size from 10 nm to 1 micrometer.

14. The improvement as defined in claim 13, wherein said metal oxide powder is said $CeO_2$.

15. The improvement as defined in claim 12, wherein the polishing composition is an aqueous suspension of the metal oxide powder.

16. The improvement as defined in claim 15, further comprising storing a washer fluid including the cleaning agent and the water in a container in the motor vehicle before the applying of the cleaning agent and the water to the glass window and adding said aqueous suspension to the washer fluid so that the aqueous suspension of the metal oxide powder is blown on the glass window at the same time as the cleaning agent and the water is applied to the glass window.

17. The improvement as defined in claim 12, wherein said polishing composition consists of said metal oxide powder and said metal oxide powder consists essentially of cerium oxide powder.

18. The improvement as defined in claim 12, wherein said blowing of the polishing composition is performed at the same time as said applying of the cleaning agent and the water to the glass window with said wiper apparatus.

19. The improvement as defined in claim 12, wherein said blowing of the polishing composition on the glass window and said applying of the cleaning agent and the water to the glass window are performed at different times.

20. The improvement as defined in claim 12, further comprising storing a washer fluid including the cleaning agent and the water in one container in the motor vehicle and storing the polishing composition in another separate container in the motor vehicle prior to the applying of the cleaning agent and the water to the glass window and the blowing of the polishing composition on the glass window.

21. In a process for cleaning a glass window of a motor vehicle with a wiper apparatus having a wiper, said process comprising the steps of applying a cleaning agent and water to said glass window and moving said wiper over said glass window with said wiper apparatus to at least partially clean said glass window with the cleaning agent and the water, the improvement comprising the steps of:

a) applying an aqueous suspension of a metal oxide powder to said glass window; and b) cleaning said glass window with said aqueous suspension of said metal oxide powder by action of said wiper together with said aqueous suspension of said metal oxide powder on said glass window, so that, when present on said glass window, a hydrophobic dirt layer formed on said glass window is removed.

22. The improvement as defined in claim 21, wherein said metal oxide powder is selected from the group consisting of $Fe_2O_3$, $Fe_3O_4$, $Al_2O_3$, $Cr_2O_3$, $CeO_2$, $ZrO_2$, $TiO_2$, $SnO_2$, $SiO_2$ powders and having a particle size from 10 nm to 1 micrometer.

23. The improvement as defined in claim 22, wherein said metal oxide powder is said $CeO_2$.

24. The improvement as defined in claim 21, further comprising storing a washer fluid including the cleaning agent and the water in a container in the motor vehicle before the applying of the cleaning agent and the water to the glass window and adding said aqueous suspension to the washer fluid in the container so that the aqueous suspension of the metal oxide powder is applied to the glass window at the same time as the cleaning agent is applied to the glass window.

25. The improvement as defined in claim 21, further comprising storing a washer fluid including the cleaning agent and the water in one container in the motor vehicle and storing the aqueous suspension in another separate container in the motor vehicle prior to the applying of the cleaning agent and the water to the glass window and the aqueous suspension on the glass window.

26. The improvement as defined in claim 21, wherein the aqueous suspension is distributed manually on a wiper lip of a wiper blade of the wiper from one of a flask and a tube.

* * * * *